(12) United States Patent
Takahashi

(10) Patent No.: US 6,296,844 B1
(45) Date of Patent: Oct. 2, 2001

(54) ASIALOCYTOKINES AND TREATMENT OF LIVER DISEASE

(75) Inventor: Hiroshi Takahashi, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/302,765

(22) Filed: Apr. 30, 1999

Related U.S. Application Data

(63) Continuation-in-part of application No. 08/721,828, filed on Sep. 27, 1996, now abandoned.
(60) Provisional application No. 60/004,357, filed on Sep. 27, 1995.

(51) Int. Cl.$^7$ .......................... A61K 38/00; A61K 38/16; A61K 38/21
(52) U.S. Cl. ........................... 424/85.6; 424/85.1; 514/2; 514/8
(58) Field of Search .......................... 514/2, 8; 424/85.1, 424/85.6

(56) References Cited

U.S. PATENT DOCUMENTS

| | | | |
|---|---|---|---|
| 4,061,538 | 12/1977 | Dorner et al. | 195/29 |
| 4,184,917 | 1/1980 | Dorner et al. | 435/68 |
| 5,346,696 | 9/1994 | Kim et al. | 424/85.4 |
| 5,378,605 | 1/1995 | Feitelson et al. | 435/5 |

FOREIGN PATENT DOCUMENTS

| | | | |
|---|---|---|---|
| WO 92/22310 | 12/1992 | (WO) | A61K/37/02 |
| WO 94/27556 | 12/1994 | (WO) | |
| WO 95/18636 | 7/1995 | (WO) | A61K/47/48 |

OTHER PUBLICATIONS

Behr et al., "Efficient Gene Transfer into Mammalian Primary Endocrine Cells with Lipopolyamine–coated DNA", Proc. Natl. Acad. Sci. USA 86:6982–6986, 1989.
Biessen et al., "Synthesis of Cluster Galactosides with High Affinity for the Hepatic Asialoglycoprotein Receptor", J. Med. Chem. 38:1538–1546, 1995.
Biessen et al., "Specific Targeting of the Antiviral Drug 5–Iodo 2'–deoxyuridine to the Parenchymal Liver Cell Using Lactosylated poly–L–lysine", Journal of Hepatology 21:806–815, 1994.
Biessen et al., "Cholesterol Derivative of a New Triantennary Cluster Galactoside Directs Low– and High–Density Lipoproteins to the Parenchymal Liver Cells", Biochem. J. 302:283–289, 1994.
Bijsterbosch et al., "Uptake of Lactosylated Low–density Lipoprotein by Galactose–specific Receptors in Rat Liver", Biochem. J. 270:233–239, 1990.
Bukowski et al., "Natural Killer Cell Depletion Enhances Virus Synthesis and Virus–induced Hepatitis In Vivo", The Journal of Immunology 131:1531–1538, 1983.
Dragsten et al., "Drug Delivery Using Vesicles Targeted to the Hepatic Asialoglycoprotein Receptor", Biochimica et Biophysica Acta 926:270–279, 1987.
Fallon et al., "Receptor–mediated Endocytosis and Targeted Drug Delivery", Hepatology 5:899–901, 1985.
Fiume et al., "Targeting of Antiviral Drugs by Coupling with Protein Carriers", FEBS Letters 153:6–10, 1983.
Ishihara et al., "Specific Uptake of Asialofetuin–tacked Liposomes Encapsulating Interferon–γ By Human Hepatoma Cells and . . . ", Biochemical and Biophysical Research Communications 174:839–845, 1991.
Kasama et al., "Pharmacokinetics and Biologic Activities of Human Native and Asialointerferon–βs", Journal of Interferon and Cytokine Research 15:407–415, 1995.
Kim et al., "Hepatitis G Virus (HGV), A New Hepatitis Virus Associated With Human Hepatitis", Journal of Hepatology 23(S1):78, 1995, abstract GS 6/35.
McIntyre et al., "Blastogenesis of Large Granular Lymphocytes in Nonlymphoid Organs", Journal of Leukocyte Biology 43:492–501, 1988.
McIntyre et al., "Accumulation of Natural Killer and Cytotoxic T Large Granular Lymphocytes in the Liver During Virus Infection", J. Exp. Med. 164:1667–1681, 1986.
Merwin et al., "Targeted Delivery of DNA Using YEE (GalNAcAH)$_3$, a Synthetic Glycopeptide Ligand for the Asialoglycoprotein Receptor", Bioconjugate Chem. 5:612–620, 1994.
Mumtaz et al., "Design of Liposomes for Circumventing the Reticuloendothelial Cells", Glycobiology 1:505–510, 1991.
Nakamoto et al., "Organ Distribution of Asialo–Red Blood Cell Ghosts: an Attempt at Targeting to the Liver", Acta Med. Okayama 40:61–64, 1986.
Nishikawa et al., "Molecular Design of Protein Derivatives Targeted to the Liver Via The Asialoglycoprotein . . . ", Proceed. Intern. Symp. Control. Rel. Bioact. Mater., 22(1995), Controlled Release Society, Inc. 502–503.
Schouten et al., "Development of Lipoprotein–like Lipid Particles for Drug Targeting: Neo–high Density Lipoproteins", Molecular Pharmacology 44:486–492, 1993.
Treichel et al., "Autoantibodies Against the Human Asialoglycoprotein Receptor: Effects of Therapy in Autoimmune and Virus–induced Chronic Active Hepatitis", Journal of Hepatology 19:55–63, 1993.
Van Berkel et al., "Specific Targeting of High Density Lipoproteins to Liver Hepatocytes by Incorporation of a Tris–Galactoside–terminated Cholesterol Derivative", The J.of Biological Chemistry 260:12203–12207, 1985.
Van Der Sluijs et al., "Drug Targeting to the Liver with Lactosylated Albumins: Does the Glycoprotein Target the Drug or Is the Drug Targeting the Glycoprotein?", Hepatology 6:723–728, 1986.

Primary Examiner—Prema Mertz
Assistant Examiner—Joseph F. Murphy
(74) Attorney, Agent, or Firm—Fish & Richardson, P.C.

(57) ABSTRACT

The invention features methods for treating liver disease (e.g., viral hepatitis) by administering an asialocytokine (e.g., asialointerferon). The invention also includes methods of targeting a glycoprotein to a hepatocyte and a composition containing an asialocytokine.

23 Claims, 9 Drawing Sheets

SEQUENCE LISTING

<160> NUMBER OF SEQ ID NOS: 8

<210> SEQ ID NO 1
<211> LENGTH: 29
<212> TYPE: DNA
<213> ORGANISM: Human hepatitis B virus

<400> SEQUENCE: 1
tgcgggtcac catattcttg ggaacaaga                              29

<210> SEQ ID NO 2
<211> LENGTH: 33
<212> TYPE: DNA
<213> ORGANISM: Human hepattitis B virus

<400> SEQUENCE: 2
agtctagact ctgcggtatt gtgaggattc ttg                         33

<210> SEQ ID NO 3
<211> LENGTH: 32
<212> TYPE: DNA
<213> ORGANISM: Rattus rattus

<400> SEQUENCE: 3
atctggcacc acaccttcta caatgagctg cg                          32

<210> SEQ ID NO 4
<211> LENGTH: 32
<212> TYPE: DNA
<213> ORGANISM: Rattus rattus

<400> SEQUENCE: 4
cgtcatactc ctgcttgctg atccacatct gc                          32

<210> SEQ ID NO 5
<211> LENGTH: 29
<212> TYPE: DNA
<213> ORGANISM: Human hepatitis B virus

<400> SEQUENCE: 5
gagaattcaa gcctccaagc tgtgcctgg                              29

<210> SEQ ID NO 6
<211> LENGTH: 28
<212> TYPE: DNA
<213> ORGANISM: Human hepatitis B virus

<400> SEQUENCE: 6
gaaagcttct gcgacgcggc gattgaga                               28

<210> SEQ ID NO 7
<211> LENGTH: 32
<212> TYPE: DNA
<213> ORGANISM: Rattus rattus

<400> SEQUENCE: 7
atctggcacc acaccttcta caatgagctg cg                          32

<210> SEQ ID NO 8
<211> LENGTH: 32
<212> TYPE: DNA
<213> ORGANISM: Rattus rattus -continued

```
<400> SEQUENCE: 8
cgtcatactc ctgcttgctg atccacatct gc                                    32
```

ASIALOCYTOKINES AND TREATMENT OF LIVER DISEASE

CROSS REFERENCE TO RELATED APPLICATIONS

This application is a continuation-in-part of U.S. patent application Ser. No. 08/721,828, filed Sep. 27, 1996, now abandoned; which claims priority from U.S. Provisional Application Ser. No. 60/004,357, filed Sep. 27, 1995.

STATEMENT AS TO FEDERALLY SPONSORED RESEARCH

This invention was made with government support under National Institutes of Health grants CA57584 and NIDDK4331. The Government has certain right in the invention.

BACKGROUND OF THE INVENTION

Hepatitis B virus (HBV) infection is a worldwide health problem. It causes a wide spectrum of pathologies ranging from inapparent infection to fatal hepatocellular diseases (Tiollais et al., Nature 317:489, 1985). The HBV virion is composed of an envelope, which carries the hepatitis B surface antigen (HBsAg), and a nucleocapsid. The nucleocapsid encloses a circular, partially double-stranded 3.2 kb DNA, which replicates via a RNA intermediate. The nucleocapsid is formed by the hepatitis B core antigen. When virions are present in the blood, an additional soluble antigen related to the nucleocapsid, the hepatitis B e antigen (HBeAg), is generally detected in the serum. Several studies have suggested that HBV is not directly hepatocytopathic and that host immune response to viral antigens presented on the surface of infected liver cells may play an important role in pathogenesis (Mondelli et al., *J. Immunol.* 129:2773, 1982; Mondelli et al., *Arch. Pathol. Lab. Med.* 112:489, 1988; Chisari et al., *Microb. Pathog.* 6:311, 1989).

The lack of suitable animal models for hepatitis B has hindered understanding of the molecular mechanisms responsible for hepatocyte death and viral clearance (Ochiya et al., *Proc. Natl. Acad. Sci. USA* 86:1875, 1989; Gripon et al., *J. Virol.* 62:4136, 1988). Germ-line transgenic mouse models have been produced to investigate the pathogenesis of HBV infection, but these animals are immunologically tolerant to HBV antigens and do not spontaneously develop hepatitis (Moriyama et al., *Science* 248:361, 1990). Hepatitis must be induced in these animals by a complicated, multistep process involving, e.g., priming lymphocytes with HBV proteins in syngeneic animals and adoptive transfer of the primed cells in vivo (Moriyama et al., supra; Ando et al., *J. EXP. Med.* 178:1541, 1993).

SUMMARY OF THE INVENTION

The invention is based, in part, on the discovery that asialo-interferonβ (asialo-IFN-β) effectively inhibits hepatitis B virus (HBV) replication in hepatocytes. Surprisingly, this level of inhibition achieved was higher than that achieved with native interferon-β, a result contrary to the previous understanding that asialo-interferon-β is less effective than native interferon-β in inhibiting virus replication in hepatocytes.

Accordingly, the invention features a method of treating viral hepatitis in a mammal (e.g., a human) by administering to the mammal a composition which includes a therapeutic amount of an asialo-interferon (e.g., asialo-IFN-alpha, asialo-IFN-β, or asialo-IFN-gamma). The method optionally includes a step of confirming that the mammal has viral hepatitis, e.g., hepatitis caused by hepatitis B virus infection or hepatitis C virus infection.

The optional confirming step can include measuring the level of hepatitis virus replication in the mammal. The level of virus replication can be measured by any means well known in the art, including hepatitis virus-specific polymerase chain reaction or by detecting hepatitis viral antigen (hepatitis B virus e antigen) in a bodily fluid (e.g., blood) of the mammal.

The composition can be administered via any suitable route, including subcutaneously, intramuscularly, intraarterially, or intravenously. In addition, the therapeutic amount can be about, e.g., 0.02 to 200 μg/kg body weight/day, 30 to 75 μg/kg body weight/day, or alternatively, 10,000 to 200,000 IU/kg body weight/day.

The composition can further include a pharmaceutically acceptable excipient, such as dextrose, an albumin, sodium chloride, a sodium phosphate, or water.

In another aspect, the invention features a method of targeting a glycoprotein to a hepatocyte by providing an asialoglycoprotein produced by removing sialic acid residues from a glycoprotein; and contacting the asialoglycoprotein with the hepatocyte. Among the glycoproteins that can be targeted to hepatocytes in this manner are IL-1, IL-3, IL-4, IL-5, IL-6, IL-7, IL-9, IL-10, IL-12, IL-13, IL-14, IL-15, erythropoietin, fibroblast growth factor, granulocyte-macrophage colony stimulating factor (GM-CSF), gamma interferon, tumor necrosis factor-β, leukemia inhibitory factor, macrophage colony stimulating factor (M-CSF), macrophage migration inhibitory factor, nerve growth factor, osteostatin M, platelet-derived growth factor, stem cell factor, thrombopoietin, vascular endothelia growth factor, or hepatocyte growth factor. The hepatocyte to be targeted can be within a liver, and the liver can be within a mammal (e.g., a human). The asialoglycoprotein can be contacted with the hepatocyte by intravenous, intraarterial, subcutaneous, or intramuscular injection of the asialoglycoprotein into the mammal.

The invention also features a composition including asialoglycoprotein produced by removing sialic acid residues from a glycoprotein, where the glycoprotein is interleukin-1 (IL-1), IL-3, IL-4, IL-5, IL-6, IL-7, IL-9, IL-10, IL-12, IL-13, IL-14, IL-15, erythropoietin, fibroblast growth factor, granulocyte-macrophage colony stimulating factor (GM-CSF), gamma interferon, tumor necrosis factor-β, leukemia inhibitory factor (LIF), macrophage colony stimulating factor (G-CSF), macrophage migration inhibitory factor, nerve growth factor, osteostatin M, platelet-derived growth factor, stem cell factor, thrombopoietin, vascular endothelia growth factor, or hepatocyte growth factor. The invention also features a method for preparing a medicament, e.g., a medicament for treatment of a liver disorder (e.g., hepatitis) by admixing an asialoglycoprotein with a pharmaceutically acceptable carrier. The composition can further include a pharmaceutically acceptable excipient.

The methods and compositions of the invention can be used to deliver a glycoprotein to hepatocytes, including the delivery of IFN, in its asialo form, to treat viral hepatitis. These asialo glycoproteins are expected to have a higher specific activity in the liver than the native glycoproteins when administered to a patient. The use of other glycoprotein cytokines for treatment of specific diseases are also well known. For example, asialo-IL-1 can be used to treat anemia, as can asialo-IL-3, asialo-IL-6, and asialo-erythropoietin. Asialo-IL-7 and asialo-IL-10 can be used to stimulate the growth and differentiation of T cells. Asialo-IL-12 can be used to activate natural killer cells. Asialo-GM-CSF and asialo-G-CSF can be used to activate and proliferate macrophages.

In addition, asialo-IL-1 can be used to treat fulminant or subacute hepatitis. Asialo-IL-3 can be used to treat pancytopenia. Asialo-IL-6 can be used to treat fulminant hepatitis or acute exacerbation of chronic active hepatitis, or can be used to produce acute phase reactants for host defense. Asialo-IL-10 can be used to treat autoimmune hepatitis or primary biliary cirrhosis. Asialo-IL-12 can be used to treat hepatocellular carcinoma, hepatic metastatic tumors, HBV infection, hepatitis C virus infection, AIDS, or parasitic infections. Asialo-GM-CSF can be used to treat malignant tumors or leukemia. Hepatocyte growth factor can be used to treat hepatic cirrhosis, liver fibrosis, or chronic hepatitis.

Thus, the invention also includes a method of treating anemia in a mammal by providing a composition having a therapeutic amount of an asialoglycoprotein, the asialoglycoprotein being produced by removing sialic acid residues from a glycoprotein (e.g., IL-1, IL-2, or erythropoietin; and by administering to the mammal the composition.

Also included in the invention is a method of stimulating growth or differentiation of a T cell by providing an asialoglycoprotein produced by removing sialic acid residues from a glycoprotein (e.g., IL-7 or IL-10); and contacting the T cell with the asialoglycoprotein. The T cell can be within a mammal, and the contacting step can include administering to the mammal a composition comprising the asialoglycoprotein.

The invention also includes a method of stimulating growth or differentiation of a macrophage by providing an asialoglycoprotein produced by removing sialic acid residues from a glycoprotein (e.g., GM-CSF or M-CSF); and contacting the macrophage with the asialoglycoprotein. The macrophage can be within a mammal, and the contacting step can include administering to the mammal a composition comprising the asialoglycoprotein.

In yet another aspect, the invention includes a method of treating hepatitis in a mammal (e.g., a human) by providing an asialoglycoprotein (e.g., IL-1, IL-6, IL-10, IL-12, or hepatocyte growth factor) produced by removing sialic acid residues from a glycoprotein; and administering to the mammal a therapeutic amount of the asialoglycoprotein

DETAILED DESCRIPTION OF THE INVENTION

Figure 1:
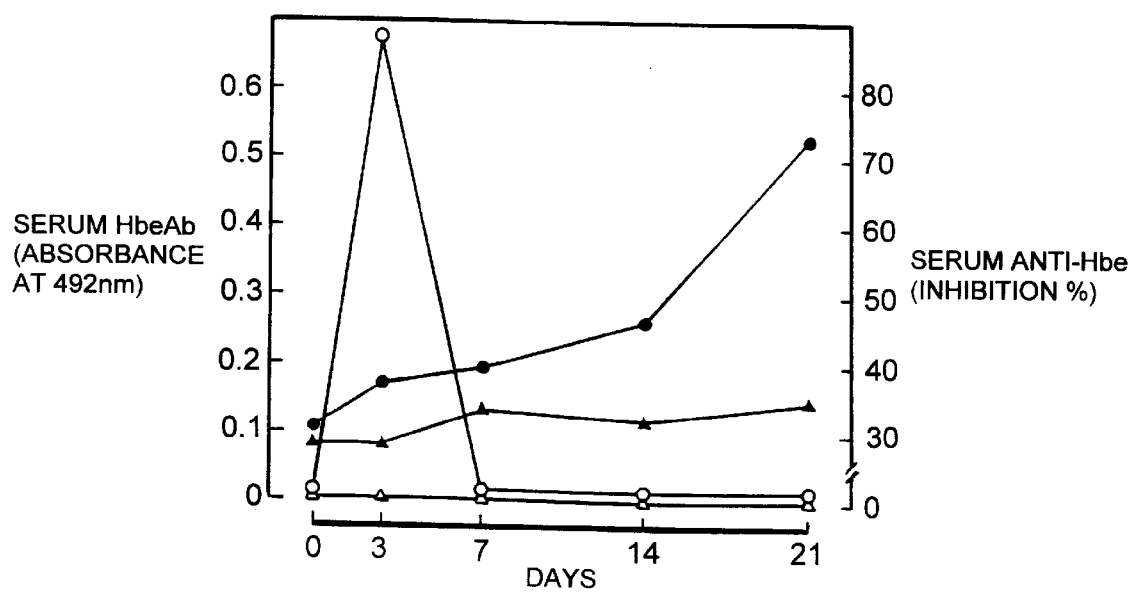
FIG. 1 is a graph depicting the results of an analysis of serum HBeAg level (open symbols) and anti-HBe antibody titer (closed symbols) in rats transfected with pHBV-HTD (circles) or pGEM-7Zf(+) (triangles). The relative concentrations of HBeAg and anti-HBe are given by $A_{492}$ and percent inhibition, respectively, as described herein. Specimens whose $A_{492}$ value is equal to or greater than the cutoff value of 0.065 (mean of the negative control plus the factor 0.06) are considered to be positive for HBeAg, and those with a percent inhibition value equal to or greater than 50% are considered to be positive for anti-HBe.

The invention relates to the use of asialo-interferon-β to treat viral hepatitis. It is believed that asialo-interferon-β is more effective than native interferon-62 in the treatment of viral hepatitis because of the prevalence of asialoglycoprotein receptors on hepatocytes.

Since the carbohydrate chain of IFN-β has an extended conformation and is linked to IFN-β at some distance from the portion of IFN-β that interacts with the IFN-α/β receptor (Karpusas et al., *Proc. Natl. Acad. Sci USA* 94:11813–11818, 1997), asialo-IFN-β may be able to associate with the asialoglycoprotein and IFN receptors simultaneously. This is so because the portion of the asialo-INF-β that binds to the asialoglycoprotein receptor is located at the end of a carbohydrate chain, which has an extended conformation, and thus is spatially separated from the portion of the asialo-IFN-β that binds to the IFN-α/β receptor. Therefore, the asialo-carbohydrate moiety in the asialo-INF-β molecule might not interfere with binding of the asialo-INF-β to the INF-α/β receptor.

In addition, the binding of asialo-IFN-β to the asialoglycoprotein receptor may increase the concentration of asialo-INF-β in the vicinity of the IFN-α/β receptor, thereby facilitating binding to the INF-α/β receptor and activation of the INF-α/β signalling pathway. Alternatively, asialo-IFN-β may bind first to the ASGP receptor, a low affinity receptor having a dissociation constant (Kd) of approximately $10^{-6}$ for biantennary and approximately $10^{-8}$ to $10^{-9}$ M for triantennary galactose-terminal oligosaccharides (Lee et al., J. Biol. Chem. 258:199–202, 1983). Biantennary asialo-INF-β bound to the asialoglycoprotein receptor may readily transfer to the IFN-α/β, which has a higher affinity (Kd $=10^{-31}$ to $10^{-12}$). Thus, it may be desirable to administer asialo-INF-β compositions that consist predominantly of biantennary complexes rather than triantennary complexes.

The human asialo-INF-β produced in human fibroblasts as described herein contain about 82% biantennary galactose-terminal oligosaccharides and about 18% triantennary galactose-terminal oligosaccharides. Various methods are known for creating INF-β having a higher or lower proportion of biantennary complexes. For example, IFN produced in fibroblasts cells has a higher proportion of biantennary complexes than IFN produced in CHO cells.

IFN receptor binding is essential for IFN-α and IFN-β to elicit their antiviral activities. Although the activation of cell surface receptors by these IFNs does not require receptor internalization, binding of IFN-α or INF-β to their intracellular receptors may trigger IFN signaling. For example, it appears that autocrine IFN-α or INF-β does not need to reach the cell surface to exert activity. Further, IFN-α incorporated into liposomes can produce significantly greater activity than free IFN-αprobably due to delivery of this cytokine to intracellular compartments. Therefore, asialo-IFN-β may be more active than native IFN-β by its ability to activate an intracellular reservoir of IFN receptors.

Previous methods for targeting drugs (e.g., polypeptide drugs) to hepatocytes have included conjugating the drug to moieties that bind to the asialoglycoprotein receptor. See, e.g., WO 95/18636; WO 91/22310; and Nishikawa et al., Proceed. Intern. Symp. Control. Rel. Bioact. Mater. 22:502–503, 1995. These procedures can substantially increase the size of the final drug molecule. In contrast, preparation of asialo-IFN by removal of sialic acid decreases the size of the IFN molecule, thereby increasing the ability of IFN to infiltrate liver tissue in vivo. This is so because exchange of substances between the blood and liver parenchyma take place at specialized capillaries called "sinusoids" that contain circular fenestrae or pores. The diameter of fenestrae ranges from 80 to 150 nm. Thus, drugs molecules whose mode of action requires passage to the liver must possess a smaller general diameter than that of the fenestrae.

Previous methods of targeting proteins to hepatocytes have involved chemical conjugation of the protein to natural asialoglycoproteins. The formation of large, multimeric macromolecules, however, may limit their accessibility to the liver in vivo because of their inability to pass through the fenestrae. Since asialo-IFNs, as defined and described herein, are prepared by removing sialic acids from glycosylated IFNs using neuraminidase, this modification of carbohydrate side chain does not increase the molecular size of IFNs and thus allows the IFN access to hepatocytes in the liver. As defined herein, an asialoglycoprotein (e.g., an asialo-IFN such as asialo-INF-β) is a protein having at least one N-linked or O-linked carbohydrate group which is free of a terminal sialic acid residue.

The examples described below establish a convenient small animal model of viral hepatitis produced by transfecting human hepatitis viral DNA into mouse hepatocytes. Also described below is the use of asialo-IFN-β in reducing hepatitis viral replication in vitro and in vivo.

Preparation of a Rat Model of Viral Hepatitis

A head-to-tail homodimer of cloned HBV (pHBV-HTD), adw sub-type, was constructed and inserted into the EcoRI site of the pGEM-72f(+) vector (Promega, Madison Wis.) as described by Blum et al., J. Virol. 65:1836, 1991 and Blum et al., Hepatology 14:56, 1991. (The cloning of the adw subtype is described in Valenzuela et al., The nucleotide sequence of the hepatitis B viral genome and the identification of the major viral genes, in Animals Virus Genetics, Fields et al., eds., Academic Press, New York, 1980, p.57.) In some cases, a head-to-tail heterodimer of HBV, adwR9, a replication-competent HBV construct similar to pHBV-HTD was used for transfection (Blum et al., J. Virol. 65:1836, 1991 and Blum et al., Hepatology 14:56, 1991).

A two-thirds hepatectomy was performed according to the Higgins-Anderson method (Higgins et al., Arch. Pathol. 12:186, 1931) 24 h before in vivo transfection, since hepatectomy increases the expression of the HBV transgene. The cloned HBV constructs were directly delivered into rat livers in vivo by using a membrane fusion-promoting cationic lipid, dioctadecylamidoglycylspermine (Behr et al., Proc. Natl. Acad. Sci. USA 86:6982, 1989). Fifty micrograms of pHBV-HTD or pGEM-7Zf(+) vector was mixed with 250 μg of the cationic lipid in 500 μl of sterile saline (0.154 M NaCl) and allowed to form a DNA-cationic lipid complex. Animals were anesthetized with ether and injected with the DNA-cationic lipid complex into the right median lobe of the liver while their portal veins were temporarily ligated by hemostatic forceps.

In addition to the above-described method, 20 μg of pHBV-HTD (or another selected DNA molecule) can be complexed with 50 μg asialofetuin-poly-L-lysine and 100 μg cationic liposome in 250 μg HBSS and injected as described above.

HBV RNA in Rat Tissues

To investigate the expression of HBV in transfected rats, total RNA was extracted from selected tissues of rats sacrificed 3 days after in vivo transfection with pHBV-HTD and amplified by RT-PCR (Chelly et al., Nature 333:859, 1988). A 659-bp PCR fragment of HBV transcript was detected in the liver but not in other tissues. In this experiment total RNA isolated from a pHBV-HTD transfected Hub-7 hepatoma cell line served as a positive control.

The level of HBV expression was measured as follows. Total RNA was extracted from the liver, heart, lung, kidney, intestine, and spleen from rats transfected with pHBV-HTD and digested with RNase-free DNase I (2 units/μg of RNA) (Promega) for 30 min. at 37° C. cDNAs were synthesized by extension of antisense primers with reverse transcriptase (BRL) in a mixture containing 2 μg of total RNA. PCR of the cDNAs was performed in a final volume of 100 μl containing 2.5 mM $MgCl_2$ and 100 pmol of each primer. The amplification cycles were 95° C. for 30 s, 50° C. for 1 min, and 72° C. for 1 min. After 35 cycles, the PCR products were separated by electrophoresis on a 1.5% agarose gel and transferred to Hybond-N+nylon membranes (Amersham). The Southern blot was hybridized with a $^{32}$P-labeled HBV-specific restriction fragment (Aat II fragment of pHBV-HTD; 3221 bp). The primers used for amplification were located within the S open reading frame of HBV (sense primer, 5'-TGCGGGTCACCATATTCTTGGGAACAAGA-3' (SEQ ID NO:1); antisense primer, 5'-AGTCTAGACTCTGCGGTATTGTGAGGATTCTTG-3' (SEQ ID NO:2), which yielded a 659-bp fragment. β-actin primers that amplified an 838-bp fragment were used as a control (sense primer, 5'-ATCTGGCACCACACCTTCTACAATGAGCTGCG-3'; SEQ ID NO:3); antisense primer, 5'-CGTCATACTCCTGCTTGCTGATCCACATCTGC-3'; SEQ ID NO:4). Total RNA obtained from a human hepatocellular carcinoma cell line (Huh-7) transfected with pHBV-HTD in vitro (Blum et al., *Hepatology* 14:56, 1991) served as a positive control for detection of HBV RNA.

HBV Virion in Rat Sera

The presence of HBV virions in serum was assessed by detecting HBV DNA by PCR after DNase I treatment of rat sera and immunoprecipitation of HBV virions with anti-HBsAg-conjugated beads. Sera were positive for virions in 18 to 21 rats. The amount of HBV detected in the serum increased during the first 3 days after transfection as assayed by increases in PCR amplifiable material detected by Southern analysis and then rapidly decreased and could no longer be detected 14 days after the transfection.

HBV virion sera was measured as follows. Sera were first treated with 20 units of DNase I (Boehringer Mannheim) per ml at 37° C. for 30 min to digest naked DNAs, such as pHBV-HTD plasmid. The HBV particles were then immunoprecipitated from the sera by using mouse anti-HBsAg antibody (5D3 monoclonal antibody) (Takahashi et al., *J. Immunol. Methods* 112:91, 1988) conjugated to azlactone-acrylamide copolymer beads (Pierce). HBV is immunoprecipitated by these antibody-conjugated beads because the complete HBV virion contains double-stranded 3.2-kb HBV DNA and carries HBsAg on its envelope. After extensive washing, HBV DNA was released from the beads by heating at 95° C. for 5 min, amplified by PCR by using the same primers described above, and hybridized to the HBV probe in a Southern analysis to confirm the specificity of the PCR products (Liang et al., *J. Clin. Invest.* 84:1367, 1989).

As an alternative, PCR analysis can be performed as follows. PCR analysis of HBV is performed in a final volume of 50 μl with 2.5 mM MgCl$_2$ and 1 μM of each primer. The cycles are 95° C. for 30 s, 50 C. for 1 min and 72° C. for 1 min. After 30 cycles, the PCR products are separated by electrophoresis on 1.5% agarose gel and transferred to Hybond-N+ nylon membranes (Amersham). The blot is hybridized with a $^{32}$P-labeled HBV-specific restriction fragment (AatII fragment of pHBV-HTD; 3221bp) for Southern analysis. The following primers, located within the core open reading frame of HBV gene, are used for the detection of HBV: sense primer, GAGAATTCAAGCCTC-CAAGCTGTGCCTGG (SEQ ID NO:5); anti-sense primer, GAAAGCTTCTGCGACGCGGCGATTGAGA (SEQ ID NO:6). These primers yield a 578 bp fragment. The following β-actin primers are used as a control: sense primer, ATCTGGCACCACACCTTCTACAATGAGCTGCG (SEQ ID NO:7); anti-sense primer, CGTCATACTCCTGCT-TGCTGATCCACATCTGC (SEQ ID NO:8). These primers yield a 1045 bp fragment.

HBV Liver DNA

HBV DNA was detected by genomic Southern analysis of liver DNA isolated from rats transfected with adwR9. DNA bands of 7.2 kb and 3.2 kb were detected in EcoRV-digested genomic DNAs by hybridization with an HBV-specific probe (Aat II fragment of pHBV-HTD). The 7.2 kb band was also seen in the same liver DNA blots rehybridized with a vector-specific probe [pGEM-7Zf(+) DNA digested by BamHI], but the 3.2 kb band was not detectable. Since both the HBV genome (adw subtype; 3.2 kb) and the adwR9 HBV constructs (7.2 kb) have a single EcoRV site (Blum et al., *Hepatology* 14:56, 1991), the observed 3.2 kb band was not derived from the digested adwR9. These data confirm that HBV DNA was produced and present in an unintegrated form in the liver. In addition, the HBV DNA was detected at a similar intensity on days 1, 2, and 3, although the adwR9 plasmid DNA in the liver rapidly decreased between day 1 and day 3. Thus, the presence of 3.2 kb HBV DNA after the clearance of the adwR9 construct from the liver indicates that HBV production may have been mediated by its own replication.

Genomic Southern analysis was performed as follows. Rat livers transfected with a head-to-tail heterodimer of HBV, adwR9, were used for analysis. DNA was extracted from the livers, digested with EcoRV, which cuts the HBV genome and adwR9 at a single site, and separated by electrophoresis through a 1% agarose gel. The DNA fragments were transferred to a Southern hybridization filter and the blots were first hybridized with an HBV-specific restriction fragment (Aat II fragment of pHBV-HTD), stripped, and then rehybridized with a vector-specific restriction fragment [pGEM-7Zf(+) DNA digested with BamHI] for Southern analysis.

Serum HBeAg and Anti-HBe Antibody Response in Transfected Rats

Figure 3:
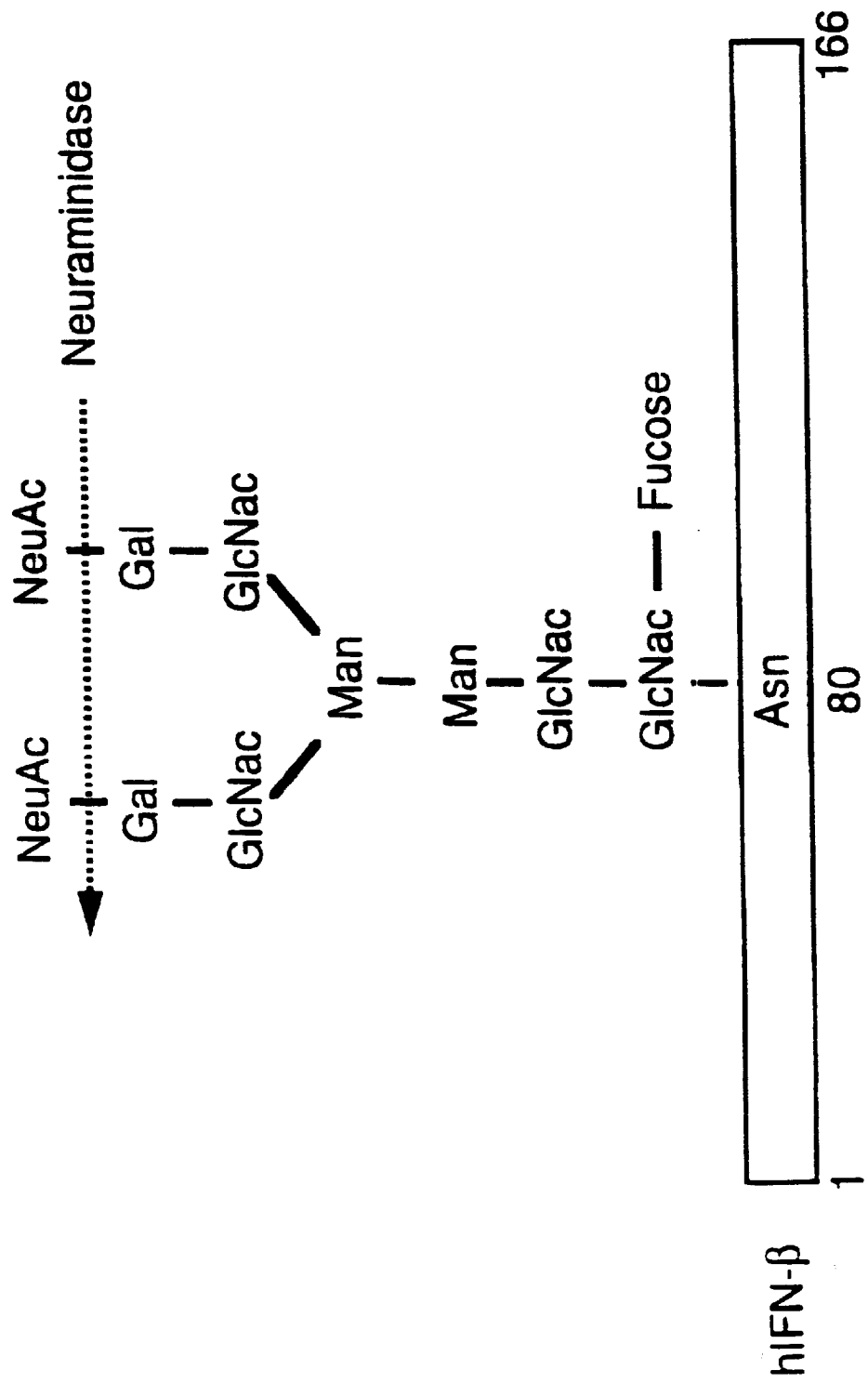
FIG. 3 is a schematic illustration of the structure of natural human IFN-β. Also illustrated are the cleavage sites of typical biantennary complex-type sugar chains of natural human IFN-βby neuraminidase. Abbreviations: Fuc, fucose; GlcNAc, N-acetylglucosamine; Man, mannose; Gal, galactose; NeuAc, N-acetylneuraminic acid.

A representative time course of serum HBeAg level and anti-HBe antibody response in pHBV-HTD-transfected rats is shown in FIG. 3. HBeAg was found in rat serum 3–7 days after liver transfection with pHBV-HTD and was followed by an increase in anti-HBe antibody titer by day 21. Neither HBeAg nor anti-HBe was found in the sera of mock-transfected rats transfected with pGEM-7Zf(+) (FIG. 1).

HBeAg and anti-HBe antibody were measured as follows. Sera were collected from tail veins of rats. The presence of HBeAg and anti-HBe antibody were determined by "sandwich" and "competitive-binding" techniques, respectively, using commercially available ELISA kits (Abbott). The relative concentration of HBeAg was represented by the absorbance value of specimens at 492 nm ($A_{492}$). The level of anti-HBe was expressed as percent inhibition calculated by using the following formula;

percent inhibition=[(mean $A_{492}$ of negative controls–$A_{492}$ of sample)/(mean $A_{492}$ of negative controls–$A_{492}$ of positive controls)]×100.

Serum Glutamic-Pyruvic Transaminase (GPT) Levels

Figure 2:
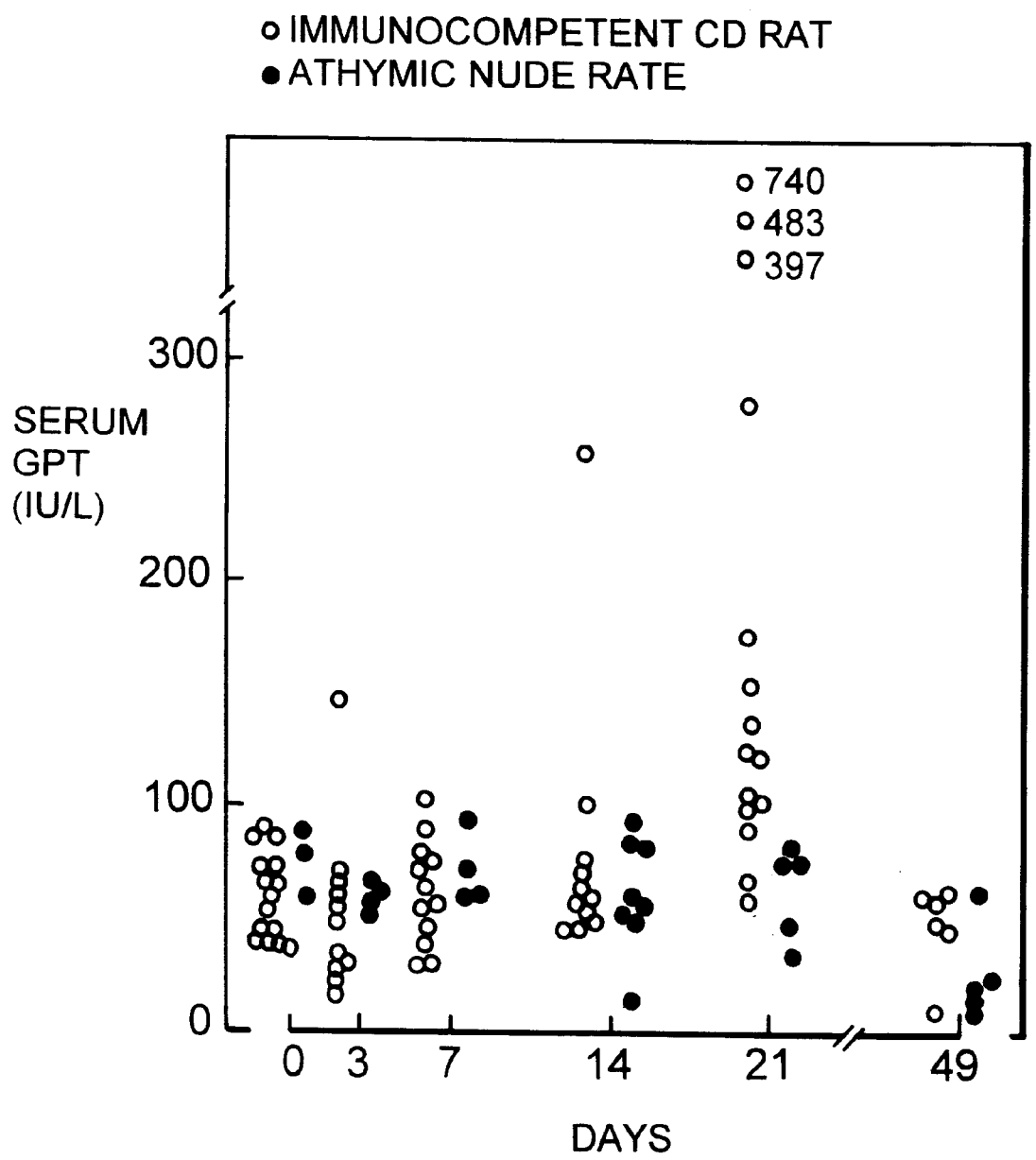
FIG. 2 is a graph illustrating serum GPT levels in normal CD rats (○) and in athymic nude rats (•) transfected with pHBV-HTD.

GPT activity in the serum was measured as an indicator of liver disease, since GPT is found primarily in the liver and released from the damaged hepatocytes. Serum GPT values were elevated in the majority of rats 2–3 weeks after HBV transfection [60 international units (IU)/l±5IU/l at day 0 and 210 IU/l±49 IU/l at day 21; mean±SEM, n=15] (FIG. 2). No serum GPT elevation was observed in the mock-transfected rats (37 IU/l±18 IU/l at day 0 and 30 IU/l±12 IU/l at day 21,n=3).

Liver Histology

Liver tissues were obtained from randomly chosen rats sacrificed 3–21 days after in vivo transfection with the pHBV-HTD, adwR9, or pGEM-7Zf(+) construct. The liver tissue histology of a rat 21 days after in vivo transfection with the pHBV-HTD construct with a serum GPT level of 483 IU/l (see FIG. 2). The parenchymal cells in the vicinity of the portal vein had disappeared and were replaced by the infiltration of lymphocytes. Other animals transfected with pHBV-HTD or adwR9 demonstrated similar histological changes. No hepatocyte death or lymphocyte infiltration was observed in the livers of mock-transfected rats.

In vivo Transfection of Athymic Nude Rats with pHBV-HTD

To see if T lymphocytes are important for the induction of liver cell injury in the experimental animal model described herein, T-lymphocyte-deficient athymic nude rats were transfected with pHBV-HTD as described above. No serum GPT elevation was observed in any of these transfected animals (FIG. 2) and their livers were histologically normal. It is interesting to note that the serum level of HBV virions increased between 7 and 21 days in these nude rats. This finding was in contrast to the serum HBV virion levels of normal rats, which rapidly decreased by 7–14 days after the transfection.

Characterization of the Model

After in vivo transfection of clone HBV DNA according to the above described technique, HBV RNA as well as 3.2-kb HBV DNA were present in the liver, and HBV virions were detected in the blood. Most importantly, HBeAg, a serological marker of active viral replication (Brechot et al., *Lancet*, ii:765, 1981; Hadziyannis et al., *Hepatology* 3:656, 1993), was found in rat sera, and its appearance was followed by an anti-HBe antibody response. These data indicate that HBV virions were actively produced and that an immune response to HBV gene products was elicited in rats transfected with the HBV constructs. Furthermore, the liver histology in these animals demonstrated severe hepatocellular injury characterized by hepatocyte death and lymphocyte infiltration when serum GPT values were elevated. Thus, HBV-induced pathogenesis in these transfected rats was characterized by the expression of HBV genes, the production of HBV virions, the increase of serum transaminase, and the characteristic histological findings. These pathological changes in rats transfected with HBV DNA are similar to those found in acute viral hepatitis induced by HBV in humans.

These studies used the head-to-tail dimer constructs of HBV (pHBV-HTD) and adwR9. These and other head-to-tail dimer constructs contain the HBV genome and endogenous viral enhancer/promoter elements that are sufficient for the production of complete virions in human hepatoma cell lines (Blum et al., *J. Virol.* 65:1836, 1991; Blum et al., *Proc Natl Acad. Sci. USA* 84:1005, 1987; Sureau et al., *Cell* 47:37, 1986; Yaginuma et al., *Proc. Natl Acad. Sci. USA* 84:2678, 1987; Yasinuma et al., *Proc. Natl Acad. Sci. USA* 84:2678, 1989), and the in vitro replication of HBV has been previously demonstrated in rat liver-derived cells (Shih et al., *Proc. Natl. Acad. Sci USA* 86:6323, 1989; Diot et al., *J. Med. Virol.* 36:93, 1992). However, there had been no previous studies to determine if the HBV gene would be expressed in rat liver in vivo after the direct transfection of these replication-competent constructs. The present data demonstrate the expression of HBV genes, the production of HBV particles, and the development of spontaneous hepatitis in rats after a single gene transfer in vivo.

In vivo Effect of Asialo IFN-$\beta$ in Athymic Nude Mice Model of HBV pHBV-HTD was complexed with asialofetuin-poly-L-lysine conjugate and cationic-liposome to make virus-like particles for liver-specific transfection (infectious liposome). The infectious liposome complex was injected in to the portal vein of nude mice via spleen. Seven days after in vivo transfection, mice were randomly selected and treated with intraperitoneal injections of physiological saline solution (PSS), IFN-$\beta$ (10,000 IU/day) or asialo IFN-$\beta$ (10,000 IU/day) for seven days.

Asialofetuin-poly-L-lysin conjugate and cationic liposome were prepared as described by Trubetskay et al. (*Bioconjugate Chem.* 3:323, 1992) and Karl et al. (*Am. J. Med. Sci.* 307:138, 1994). Since asialofetuin binds asialoglycoprotein receptor on hepatocytes and cationic liposome facilitates the fusion to cell membrane and delivery of DNA into hepatocytes, pHBV-HTD was complexed with asialofetuin-poly-L-lysine conjugate and cationic-liposome in order to accomplish liver-specific transfection. In brief, 50 $\mu$l of pHBV-HTD (400 $\mu$g/ml of DMEM), 100 $\mu$l of asialofetuin-poly-L-lysine conjugate (500 $\mu$g/ml of HBSS, pH 7.4) and 100 $\mu$l of cationic-liposome (1,000 $\mu$g/ml of HBSS, pH 7.7) were mixed in microcentrifuge tube. After 15 minute incubation at room temperature with mixing, the [asialofetuin-poly-L-lysine]-[DNA]-[cationic lipid] complex was filtered through 0.2 $\mu$m polycarbonate membrane filter (Poretics Corporation, CA) before transfection.

To produce human asialo-IFN-$\beta$, 20 mg of insoluble neuraminidase attached to beaded agarose (about 0,22 units, Sigma) was suspended in 1 ml distilled water in a microcentrifuge tube and allowed to hydrate briefly. The tube was then quick-spun and washed three times with 1 ml of sodium acetate buffer (pH 5.5) containing 154 mM NaCl and 9 mM calcium chloride. The gel (about 72 $\mu$l) was then resuspended in 150 $\mu$l of the sodium acetate buffer. Glycosylated human IFN-$\beta$ ($3 \times 10^6$ IU/vial, which was about 0.15 mg) was then suspended in 150 $\mu$l of sodium acetate buffer. The gel and IFN-$\beta$ were then mixed and incubated on a rotating platform at 37° C. for three hours. The mixture was then transferred to a Z-spin tube having a 0.2 $\mu$m filter. The asialo-IFN-$\beta$ was then separated from the neuraminidase by quick spin. Fifty microliter aliquots were made and stored at −80° C. until use.

HBV particles were produced in all nude mice by in vivo transfection using infectious liposomes. In nude mice treated with PBS, HBV viremia continued to the end of the treatment (14 days after the transfection). Sialylated natural IFN-$\beta$ (10,000 IU/mouse/day for 7 days) did not demonstrate significant anti-viral effect. In contrast, asialo IFN-$\beta$ (10,000 IU/mouse/day for 7 days) demonstrated substantial anti-viral effect.

Effect of Human Asialo IFN-$\beta$ on HBV Transfected Human Hepatoma Cells

Asialoglycoprotein receptor bearing hepatoma cell lines were identified using [$^{121}$I]-labeled asialo-orsomucoid (Schwartz et al., *J. Biol. Chem.* 256:8878, 1981). One asialoglycoprotein receptor expressing cell line Hep G2 (American Type Culture Collection; Bethesda, Md.: ATCC HB8065) was selected for transfection with HBV. Hep G2 cells were transfected with pHBV-HTD as described below.

To examine the effect of asialo IFN-$\beta$ and natural IFN-$\beta$ on HBV-transfected HepG2 cells, $2 \times 10^5$ transfected cells were treated with either human natural IFN-$\beta$ (1,000 IU/ml), asialo IFN-$\beta$ (1,000 IU/ml), or saline for 48 hours. Cytotoxicity was monitored using a calorimetric MTT cell proliferation assay as described by Mosmann (*J. Immunol. Meth.* 65:55, 1983).

Asialo IFN-$\beta$ is More Effective than the Natural IFN-$\beta$

Both asialo IFN-$\beta$ and natural IFN-$\beta$ were found to reduce HBV production by HBV transfected Hep G2 cells. However, asialo IFN-$\beta$ was found to be more effective than natural IFN-$\beta$. Asialo IFN-$\beta$ reduced HBV production more than 5-fold, compared to control cells, while natural IFN-β reduced HBV production only 1.5 to 2-fold. Moreover, asialo IFN-β reduced HBsAg production by HBV transfected HepG2 cells 26–38%, while natural IFN-β reduced HBsAG production 33–40%.

TABLE 1

|  | HBsAg (ng/ml) | | |
| --- | --- | --- | --- |
|  | 0 hr | 48 hr | 72 hr |
| Saline | 0.018 ± 0.006 | 6.934 ± 0.175 | 14.530 ± 0.280 |
| IFN-β (1,000 IU/ml) | 0.029 ± 0.003 | 2.747 ± 0.090* | 3.830 ± 0.266** |
| AS-IFN-β (1,000 IU/ml) | 0.042 ± 0.008 | 2.618 ± 0.093* | 3.830 ± 0.266** |

NOTE:
Six hours after transfection, saline, IFN-β or asialo-IFN-β was added to culture medium (0 hr). Production of HBsAg from transfected HepG2 cells was significantly inhibited by IFN-β and AS-IFN-β by 48 hr treatment (*: P = 0.00004 vs. saline, **: P = 0.00004 vs. saline and P = 0.015 vs. IFN-β respectively by Student's t test).

The effect of asialo IFN-β and natural IFN-β on pHBV-HTD transfected SK-HEP cells was examined. These cells lack the asialoglycoprotein receptor. For these cells, asialo IFN-β was no more effective than natural IFN-β.

The following methods were used in the experiments described in this section.

For these experiments, human asialo IFN-β was prepared from natural glycosylated IFN-β as described above. HBV virion production by HBV-transfected HepG2 cells was measured as described above. HBV surface antigen (HBsAg) was examined using a enzyme-linked immunosorbent assay (AUSZYME, Abbot Laboratories).

All cell lines were maintained in Eagle's MEM (M.A. Bioproducts; Walkersville, Md.) supplemented with 10% fetal calf serum inactivated at 56° C. for 30 min., 10 $\mu$M non-essential amino acids, 100 U/ml penicillin, and 100 $\mu$g/ml streptomycin. Cells used for in vitro testing were harvested from the monolayer cultures by treatment with 0.04% EDTA/versine buffer in the absence of trypsin for 5 min. at 37° C.

Cells were transfected with pHBV-HTD (described above) by the calcium phosphate method (*Mol. Biol. Cell.* 7:2745, 1987) using 2×10$^5$ cells and 3 $\mu$g of pHBV-HTD per 300 mm plate. After transfection, 30 $\mu$l of IFN-β (100 IU/βl) or asialo IFN-β (100 IU/$\mu$l) were applied every 6 hours for 48 hours to culture medium to a final concentration of 1,000 IU/ml. The same total volume of physiological saline was added to control cultures.

Asialo-interferon

Asialo interferon used to treat hepatitis B and other conditions can be produced by removing a terminal sialic residue from interferon which is glycosylated and normally has such a residue by virtue of it having been produced in a eukaryotic cell (see, e.g., U.S. Pat. No. 4,184,917 and references cited therein, and Kasama et al., *J. Interfer. Cyto. Res.* 15:407–415, 1995). The terminal sialic residue can be removed by, for example, mild acid hydrolysis, or treatment of native glycosylated IFN with isolated and purified bacterial or viral neuraminidase as described in Drzenieck et al., Microbiol. Immunol. 59:35, 1972. Neuraminidases are readily available from Sigma Chemical Co. (St. Louis, Mo.) as catalog nos. N 3642, N 5146, N 7771, N 5271, N 6514, N 7885, N 2876, N 2904, N 3001, N 5631, N 2133, N 6021, N 5254, and N 4883.

Native, glycosylated interferon can be isolated from human cells, which produce it naturally, or from eukaryotic cells which have been manipulated so that they express a cloned interferon gene. Methods for natural or recombinant production of interferon are generally described in U.S. Pat. Nos. 4,758,510, 4,124,702, 5,827,694, 4,680,261, 5,795,779, and 4,130,641. Alternatively, isolated and purified human interferon is available from Sigma as catalog nos. I 2396, I 2271, I 1640, and I 6507.

Animal Models

The methods described above may be used to prepare rodent models of other forms of hepatitis. Thus, other variant and mutant form of the hepatitis B virus may be used in place of adw2 variant used in the above-described experiments. Thus, the adw, adr(1), adr(2), ayr, ayw(1), ayw(2) or other variants may be used. In addition, the methods described above may also be used by those of skill in the art to prepare models of hepatitis C and hepatitis G.

Treatment with Asialo-interferon

The method described above, and other techniques known to those skilled in the art, can be used to prepare asialo forms of glycosylated cytokines. Thus, it may be possible to prepare asialo forms of interferon $\alpha_2$ or other glycosylated human interferons. The asialo-interferons can be used to treat a wide rage of hepatic diseases or other diseases requiring administration of interferon to cells bearing the asialoglycoprotein receptor including: hepatitis B, hepatitis C, renal cell carcinoma, and hepatitis G.

The removal of a terminal sialic acid residue may be a useful method for modifying a wide range of other proteins produced in eukaryotic cells (naturally or by expression of a recombinant gene). This modification should produce an asialo-protein which can be more readily taken up by cells bearing the asialoglycoprotein receptor and is thus more effective.

Asialo-INF-β inhibits HBV Replication in vitro and in vivo and is Superior to Native IFN-β.

The efficacy of asialo-IFN-β was assessed by its ability to reduce the production of intact HBV virions by Hep G2 human hepatoma cells transfected with a replication-competent HBV construct carrying a head-to-tail homodimer of the entire HBV genome (pHBV-HTD; see above). This liver cell line expresses asialoglycoprotein receptor at a level similar to normal human hepatocytes (Eisenberg et al., *J. Hepatol.* 13:305–309, 1991; and Schwartz et al., *J. Biol. Chem.* 256:8878–8881, 1981).

The experiments described below establish the asialo-INF-β is more effective in inhibiting hepatitis viral replication in hepatocytes than native IFN-β. This result concurs with the finding, also discussed below, that asialo IFN-β induced 2'-5' oligoadenylate synthetase, an indicator of the IFN antiviral cellular response, at a level significantly higher than that induced by native IFN-β.

Figure 4:
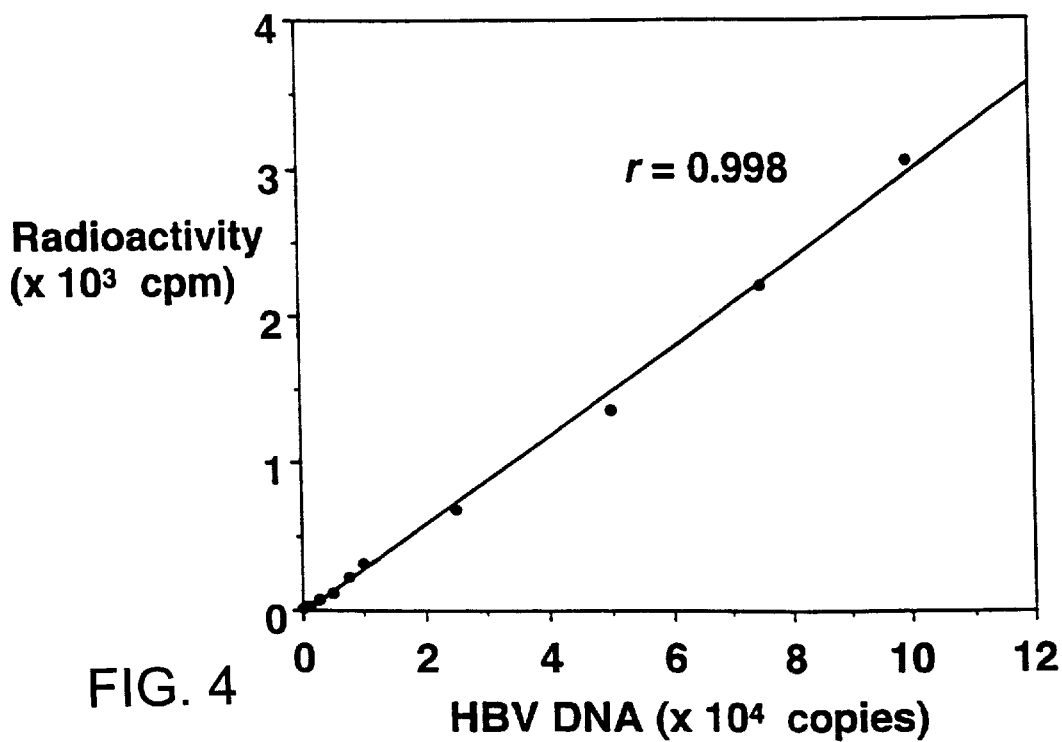
FIG. 4 is a graph of a standard curve for the quantification of HBV DNA by radioactive PCR using [alpha-$^{33}$P]-dCTP.

For quantification of the intact virions containing HBV DNA, a radioactive polymerase chain reaction (PCR) method was used. This method involved DNase I digestion of the culture supernatant and immunoprecipitation of enveloped viral particles. The quantification was validated by applying this method to a serially diluted virus DNA preparation. FIG. 4 shows a precise linear relationship (linear regression correlation coefficient; r=0.998, P<0.001) between the incorporation of [$\alpha$-$^{33}$P]-labeled dCTP into the PCR product and the known number of control HBV DNA copies. FIG. 4 also provides a standard curve for calculation of copy number of HBV DNA-containing intact virions in transfection experiments.

The methods carried out in this section were performed as follows. The human hepatoma cell lines SK-HEP-1 cells and Hep G2 cells (American Type Culture Collection, Rockville, Md.) were cultured in the presence of 5% $CO_2$ at 37° C. in Dulbecco's Modified Eagle Medium (D-MEM) (BioWhittaker, Inc., Walkersville, Md.) supplemented with 10% heat-inactivated fetal calf serum (FCS) (Sigma Chemical Co. St. Louis, Mo.), 100 μM non-essential amino acids, 100 U/ml penicillin, and 100 μg/ml streptomycin.

Human asialo-INF-β was prepared as described above.

Hepatoma cells ($2 \times 10^5$ cells) were cultured in 30 mm plastic dishes and transfected with 3 μg of pHBV-HTD using a calcium phosphate mammalian cell transfection kit (5 Prime→3 Prime, Inc.; Boulder, Colo.). Transfected cells were treated with either natural IFN-α, natural IFN-β, asialo-IFN-β, or saline (control) at 24 hrs and 48 hrs after transfection. The culture supernatant was collected at 72 hrs post-transfection. Viability of hepatoma cells treated with IFNs was assessed by means of a dye-reduction assay with 3-[4,5-dimethylthiazol-2-ol]-2,5-diphenyltetrazolium bromide (MTT) (Sigma Chemical Co.; St. Louis, Mo.).

To measure HBV production, cell culture supernatants (200 μl) were treated with 20 U/ml of DNase I (Sigma) at 37° C. for 15 minutes to degrade any plasmid or free HBV DNA. Ten microliters of EDTA (0.5 M, pH 8.0) was then added to inactivate DNase I. The enveloped virus particles were absorbed with a high affinity monoclonal antibody specific to HBV surface antigen (Takahashi et al., *Proc. Natl. Acad. Sci. USA* 92:1470–1474, 1995) which was covalently conjugated to azlactone-acrylamide copolymer beads (3M Emphaze™ Biosupport Medium AB1, Pierce, Rockford, Ill.). After extensive washing, HBV DNA was released from the beads in 50 μl of distilled water by heating at 95° C. for 10 minutes. Quantification of HBV DNA was performed by PCR using primers 5'-GAGAATTCAAGCCTCCAAGCTGTGCCTTGG-3' (SEQ ID NO:5) and 5'-GAAAGCTTCTGCGACGCGGCGATTGAGA-3' (SEQ ID NO:6). The PCR was carried out with a hot start using AmpliWax™ PCR Gem (PE Applied Biosystems, Foster City, Calif.) in a 50 μl of mixture containing 20 μl of DNA sample, 2.5 mM $MgCl_2$ with 1 μM of two primers, 0.01 mM of dNTPs, 2.5 units of Taq DNA polymerase (AmpliTaq; PE Applied Biosystems, Foster City, Calif.) and 10 μCi of [$\alpha$-$^{32}$P]-dCTP with amplification cycles of 95° C. for 30 s, 50° C. for 1 min, and 72° C. for 3 min. After 25 cycles, 10 μl of each of the PCR products were separated by electrophoresis in 6% (w/v) polyacrylamide gels. PCR product bands were located by autoradiography and excised, and the radioactivity was measured with a liquid scintillation counter (Beckman Instruments, Fullerton, Calif.). For quantification of HBV, a standard curve was constructed from PCRs with known quantities of 3.2 kb linearized HBV DNA. To ensure the absence of the transfecting plasmid in the DNA samples, PCRs were also carried out with the sense primer located in the lacZ sequence of the pGEM-7Zf(+) vector substituted for the sense primer (SEQ ID NO:5) for the HBcAg sequence. No template contamination could be detected DNase treatment.

Seven to eight week old Balb/c athymic nude (nu/nu) mice were obtained from Harlan Sprague Dawley, Inc. (Indianapolis, Ind.). Throughout the experiments, these animals were maintained under specific-pathogen-free-conditions. Mice were transfected with pHBV-HTD in vivo using a liver-specific transfection reagent that consists of a [asialofetuin-poly-L-lysine]-[HBV DNA]-[cationic liposome] ternary complex. The N-terminal modified poly (L-lysine) was conjugated to asialofetuin using conditions similar to those described for the conjugation of poly(L-lysine) to an antibody (Trubetskoy et al., *Biochim. Biophys. Acta* 1131:311–313, 1992). Fifty microliters of pHBV-HTD (400 μg/ml in D-MEM), 100 μl of asialofetuin-poly-L-lysine conjugate (500 μg/ml in Hank's balanced salt solution, pH7.4) and 100 μl of cationic-liposome containing 65 mol % 3β[N- (N',N'-dimethylamoethane) carbamyoyl] cholesterol and 35 mol % oleoylphosphatidylethanolamine (1,000 μg/ml in Hank's balanced salt solution, pH7.7) were combined in a microcentrifuge tube. After a 15 minute incubation at room temperature with mixing, the ternary complex was filtered through a 0.2 μm polycarbonate membrane filter (Poretics Corporation, Calif.) and injected into the portal vein of nude mice via the spleen. Seven days after in vivo transfection, mice were randomly selected, and their blood was sampled by periorbital bleeding. They were then treated with intraperitoneal injections of saline as placebo, mouse IFN-β or asialo-IFN-β (1,000 or 10,000 IU in 200 μl of saline/day, respectively) for seven consecutive days.

To measure 2'–5' oligoadenylate (2–5A) synthetase activity, HepG2 cells were treated with 100 IU/ml of human IFN-β or asialo-INF-β for 8, 12 or 24 hours in 24-well plastic plates. The cells were washed twice with phosphate-buffered saline, lysed in lysis buffer containing 10 mM HEPES (pH7.6), 10 mM KCl, 2 mM magnesium acetate, 7 mM 2-mercaptoethanol, and 0.5% Nonidet P-40. The cells were then sonicated for 20 seconds and centrifuged at 15,000×g for 15 min. The protein concentrations of cell lysates were determined by Bradford dye-binding procedure using Bio-Rad protein assay kit (Bio-Rad Laboratories, Hercules, Calif.). All samples were frozen at −80° C. until assayed. The level of 2–5A synthetase activity in Hep G2 cells was measured using radioimmunoassay kit (Eiken Immunochemical Laboratory, Tokyo, Japan) as described in Shindo et al., *Hepatology* 8:366–370, 1988.

Figure 6:
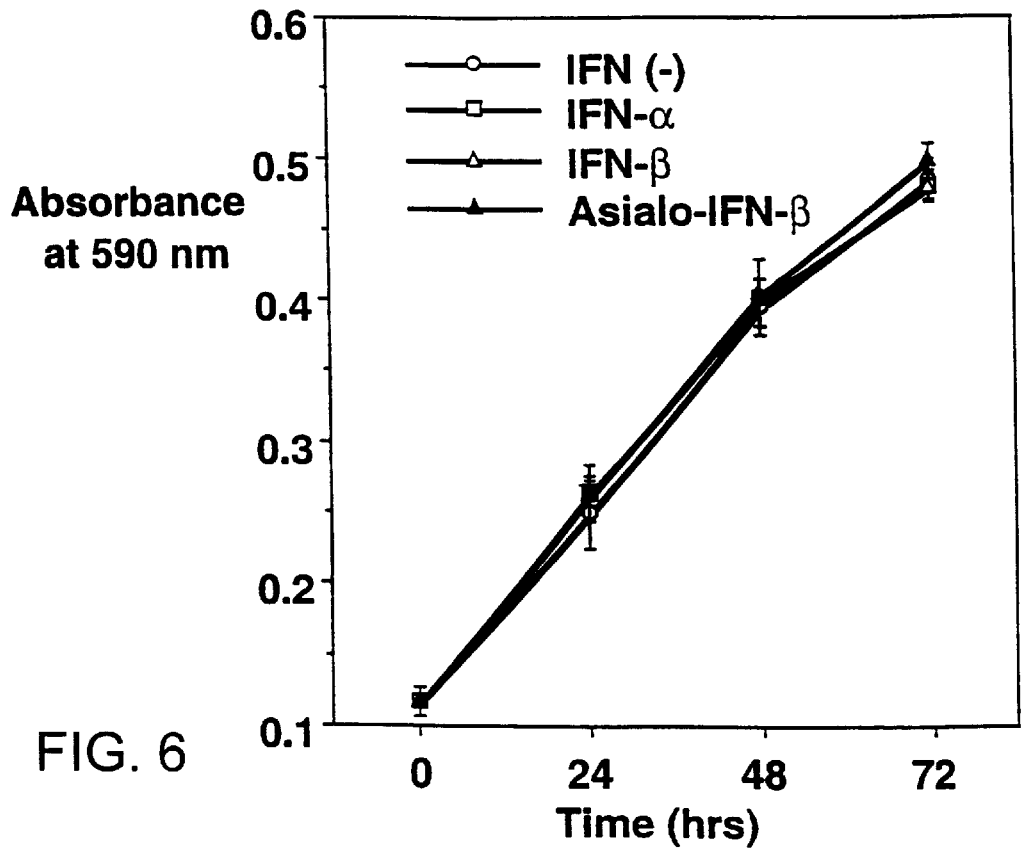
FIG. 6 is a graph of $OD_{590}$ in a cell viability assay using 3-[4,5-dimethylthiazol-2-ol]-2,5-diphenyltetrazolium bromide (MTT) versus time. Hep G2 cells were treated with 1000 IU/ml of conventional IFN-alpha, IFN-β, or asialo-IFN-β every 24 hours for 72 hours. Results are the mean plus or minus SD of values obtained in triplicate experiments.
Figure 5:
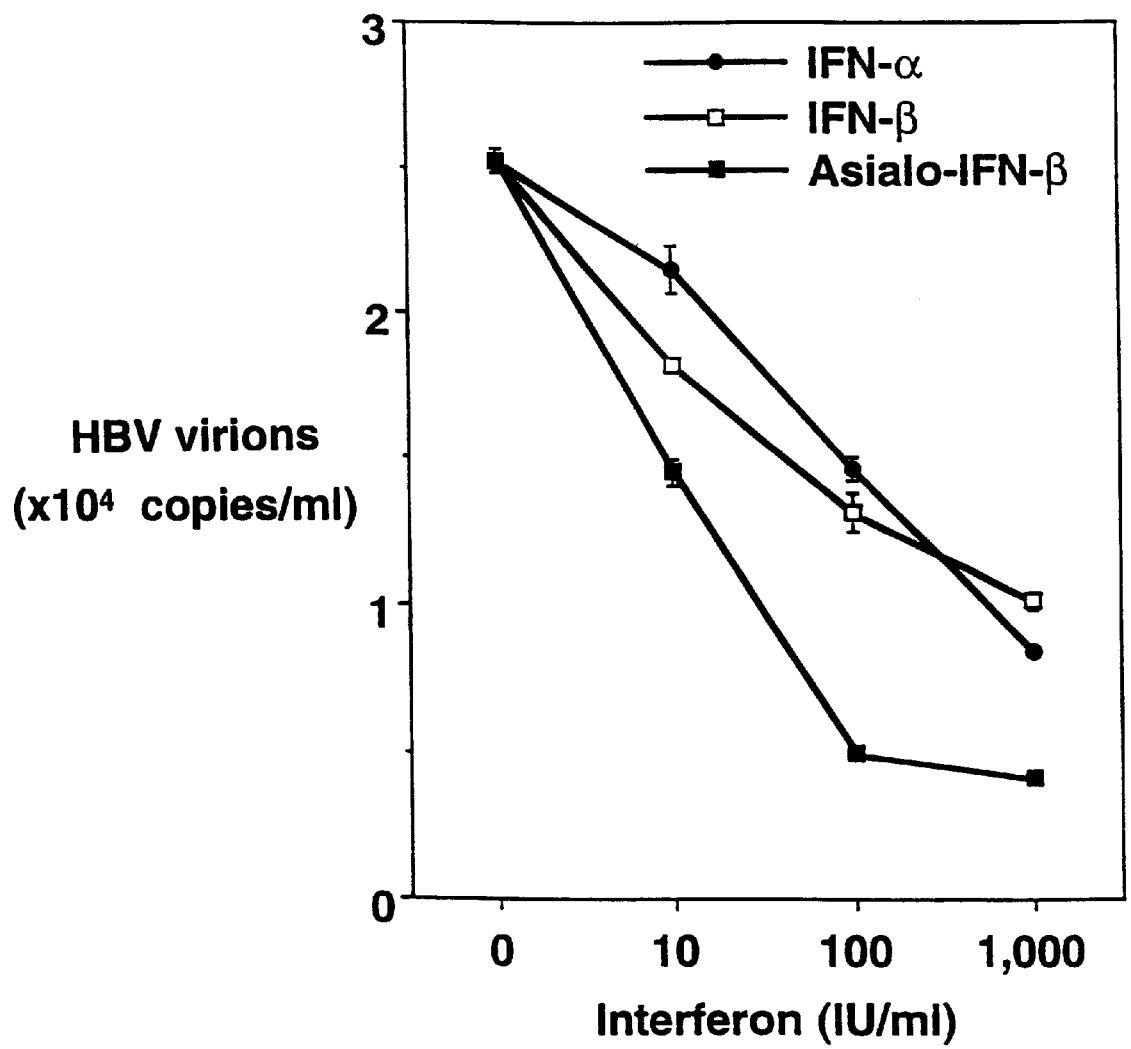
FIG. 5 is a graph of HBV copy number in a culture of HBV DNA-transfected Hep G2 cells versus interferon concentration in the culture media. HBV-transfected Hep G2 cells were treated with human natural IFN-alpha, human natural IFN-β, or asialo-IFN-β (at 10, 100, or 1000 IU/ml) every 24 hours for 48 hours. The reduced production of HBV in the culture supernatant of transfected Hep G2 cells is shown by the reduction in copy number of HBV DNA-containing virions that are present in one milliliter of the culture supernatant. Results are the mean plus or minus one standard deviation (SD) of values obtained in triplicate experiments.
Figure 7:
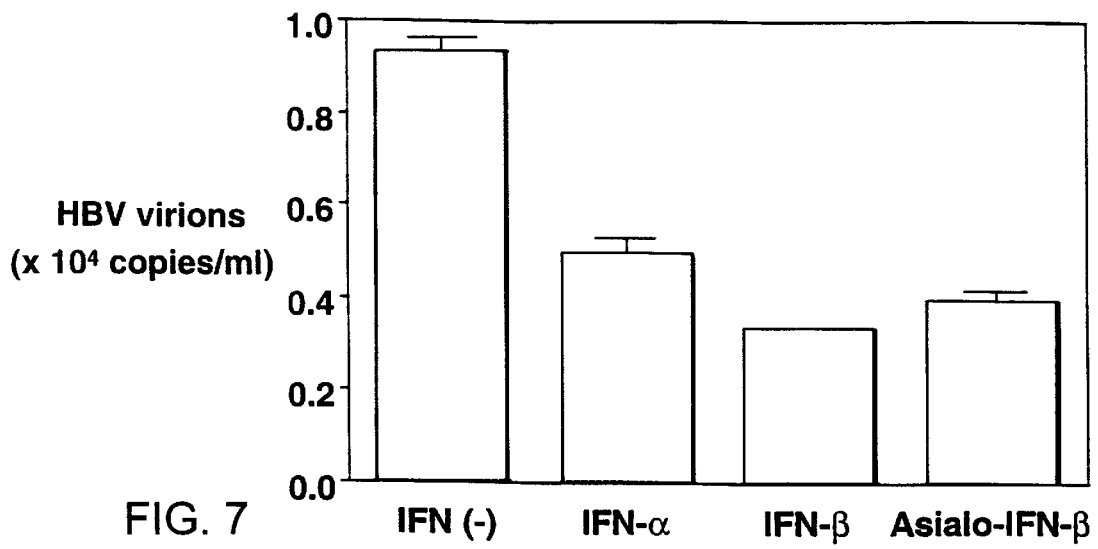
FIG. 7 is a bar graph of HBV copy number in untreated ASGP receptor-negative liver cells or the same cells treated with IFN-alpha, IFN-β, or asialo-IFN-β. SK-HEP-1 cells were treated with 1000 IU/ml of cytokine every 24 hours for 48 hours. Results are the mean plus or minus SD of values obtained in triplicate assays.

HBV-transfected Hep G2 cells were treated with asialo-IFN-β and its anti-viral effect was compared with that of conventional natural human IFN-α (Sumitomo Pharmaceutical Co., Osaka, Japan) or IFN-β (Toray Industries, Tokyo, Japan). As shown in FIG. 5, asialo-IFN-β produced a significantly greater antiviral effect than conventional IFN-α or β (P<0.001; asialo-IFN-β versus conventional IFN-α or β at 10, 100 and 1,000 IU/ml by Bonferroni t tests after significant ANOVA). At the 100 IU/ml dose, the HBV copy number under asialo-INF-β treatment was less than half of the HBV copy number under native IFN-β treatment. Thus, the asialoglycoprotein was at least twice as effective in reducing HBV replication as the native counterpart. Similar results were observed using Huh-7, another human hepatoma cell line that highly expresses asialoglycoprotein receptor. The increased inhibition of HBV by asialo-IFN-β was not due to cytotoxic effects. No cytotoxicity was observed even at the highest dose (1,000 IU/ml, every 24 hrs for 72 hrs) that was used in these experiments when examined by the MTT dye-reduction assay (FIG. 6).

Figure 11:
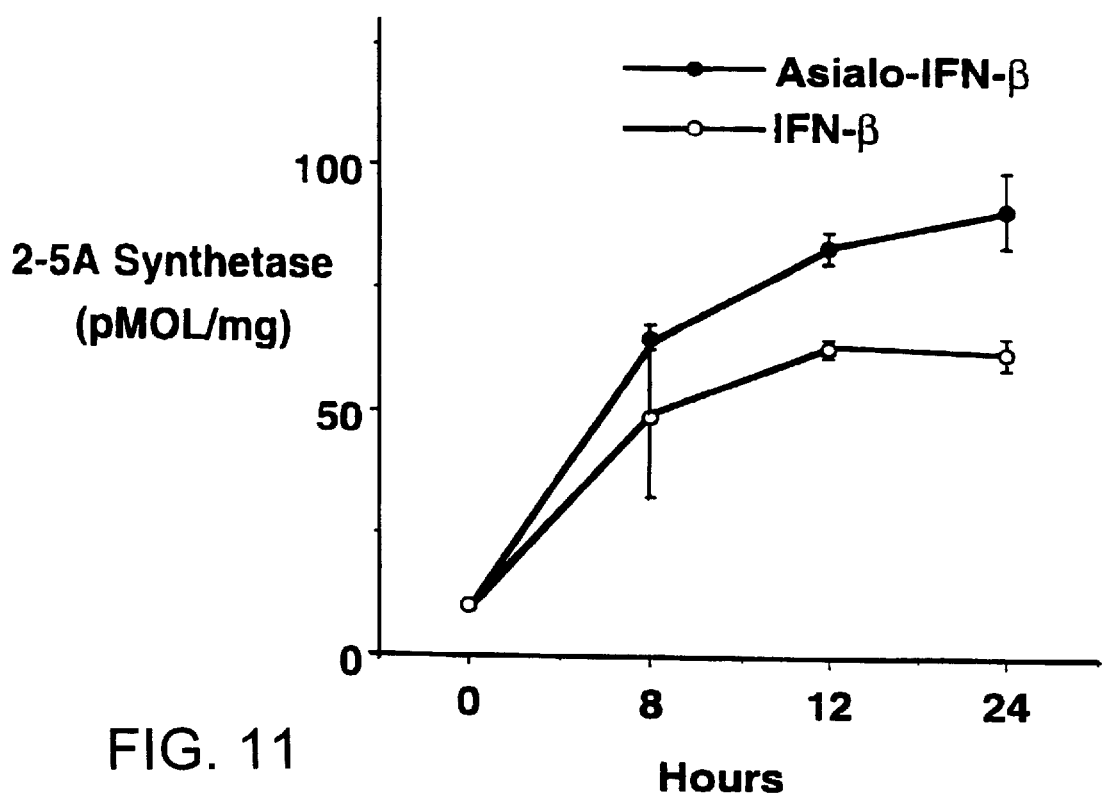
FIG. 11 is a graph of 2–5A synthetase activity in a cell culture versus number of hours of INF treatment. The open circles represent the level of 2–5A synthetase during native IFN-β treatment. The closed circles represent the level of 2–5A synthetase during asialo-IFN-β treatment.

To confirm the antiviral effect of asialo-IFN-β, 2–5A synthetase activity was measured. This IFN-induced enzyme polymerizes ATP into 2'–5' oligoadenylates which then activate a latent endoribonuclease to degrade RNAs. Since HBV replicates via an RNA intermediates, induction of 2–5A synthetase is thought to play an important role in antiviral action of IFN through its inhibition of protein synthesis and viral replication. As shown in FIG. 11, it was found that 2–5A synthetase activity in the asialo-IFN-β-treated Hep G2 cells increased at a level significantly higher than that of conventional IFN-β-treated Hep G2 cells (P=0.025 and 0.004; asialo-INF-β versus conventional IFN-β by t tests at 12 hrs and 24 hrs, respectively). Thus, augmented antiviral effect of human asialo-INF-β was confirmed by the enhanced induction of 2–5A synthetase activity.

Figure 8:
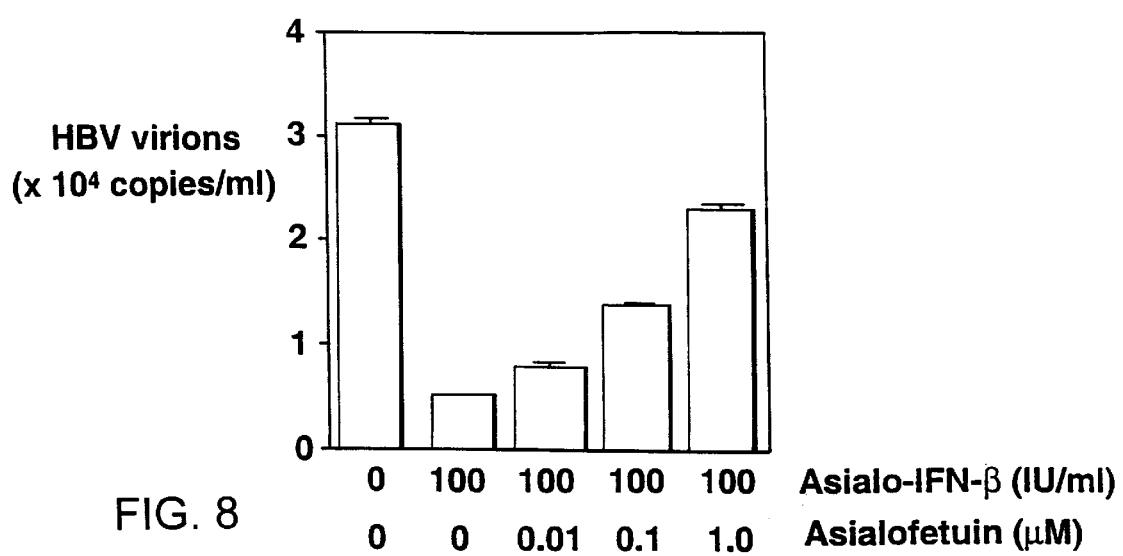
FIG. 8 is a bar graph of HBV copy number in cells treated with various concentrations of asialo-IFN-β and/or asialofetuin, a competitor for the ASGP receptor. HBV DNA-transfected Hep G2 cells were treated every 24 hours for 48 hours with 100 IU/ml of asialo-IFN-β in the presence of various concentrations of asialofetuin (0–1.0 micromolar). Results are the mean plus or minus SD of values obtained in triplicate experiments.

To determine whether or not increased drug efficacy of asialo-IFN-β was mediated by asialoglycoprotein receptor on the target cells, a competitive inhibition experiment was performed using asialofetuin as a competitive ASGP receptor inhibitor. As shown in FIG. 8, the antiviral effect of asialo-IFN-β was inhibited by asialofetuin (0.01–1.0 μM) in HBV-transfected Hep G2 cells (P<0.01 for all pairwise comparisons by Bonferroni t tests after significant ANOVA).

The importance of ASGP receptor was further investigated using a SK-HEP-1 human hepatoma cell line that is negative for asialoglycoprotein receptor. It was found that asialo-IFN-β did not exhibit an increased antiviral effect compared with conventional IFN-α or β in this asialoglycoprotein-negative cell line.

Figure 9:
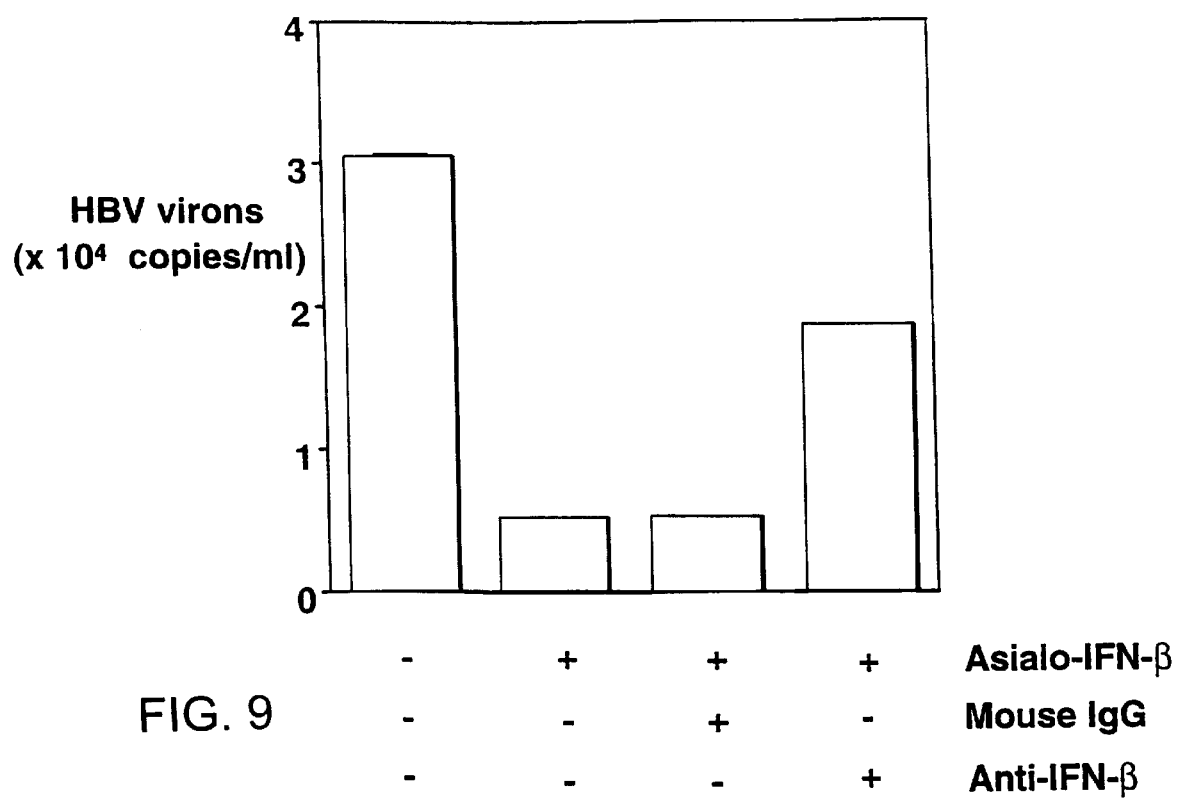
FIG. 9 is bar graph of HBV copy number in cell cultures treated with asialo-IFN-β, non-specific mouse IgG1/kappa, or a mouse antibody which neutralizes human IFN-β (B-02, IgG1/kappa, Japan Immuno-Monitoring Center, Inc., Tokyo, Japan). HBV DNA-transfected Hep G2 cells were treated every 24 hours for 48 hours with 100 IU/ml of asialo-IFN-β in the presence of one microgram/ml of B-02 antibody or non-specific mouse antibody. Results are the mean plus or minus SD of values obtained in triplicate experiments.

To examine whether the enhanced antiviral effect of asialo-IFN-β is also dependent on its binding to IFN receptor, anti-human IFN-β neutralizing antibody was used to block asialo-IFN-β binding to IFN receptor. As shown in FIG. 9, the antiviral effect of asialo-IFN-β was inhibited by this neutralizing antibody, but not by an isotype-matched non-IFN-specific mouse IgG (P<0.001, anti-IFN-62 versus no antibody or irrelevant mouse IgG; P>0.05, no antibody versus irrelevant mouse IgG by Bonferroni t tests after significant ANOVA). This result confirmed that asialo-IFN-β exerts its antiviral effect via IFN receptor signaling.

Figure 10:
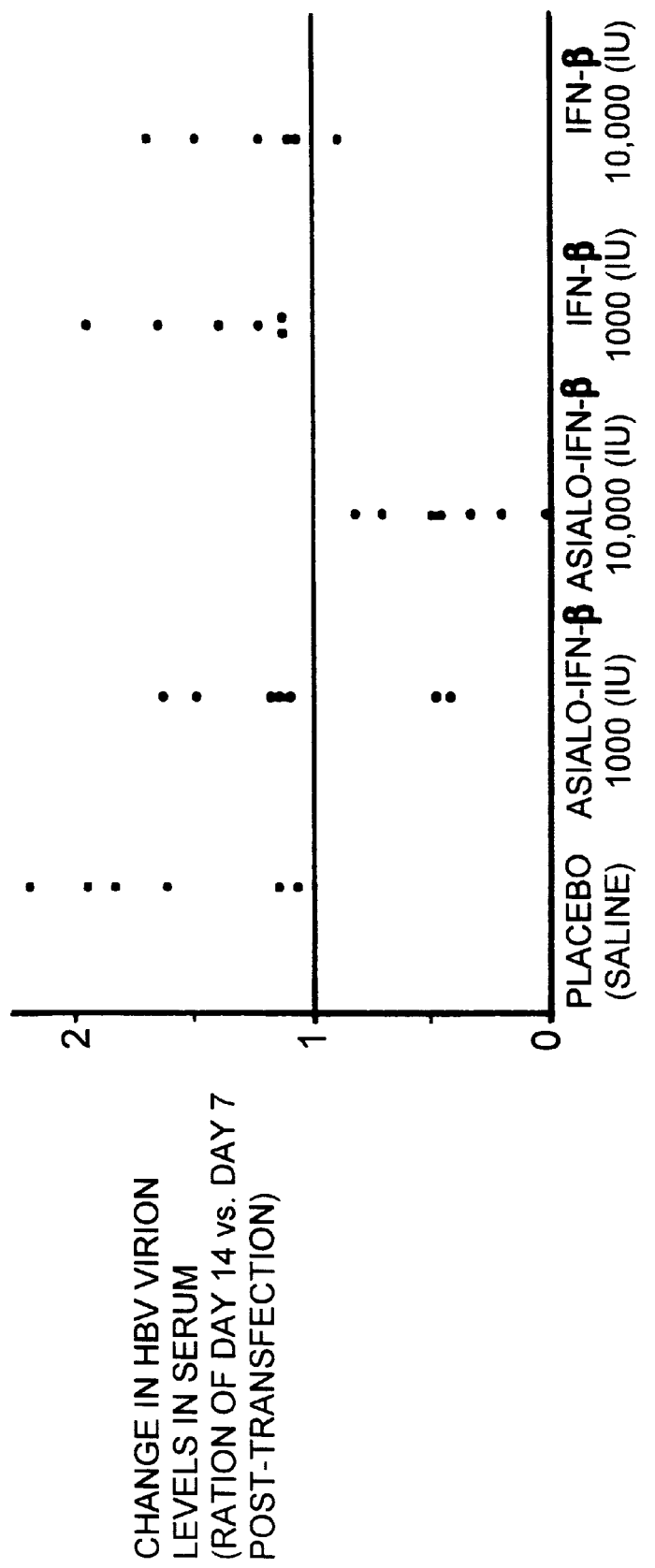
FIG. 10 is a plot of the relative change in serum HBV virion levels in HBV-transfected mice for various treatments.

The efficacy of human asialo-INF-β was again tested in vivo. In this experiment, the specificity of PCR amplifiable HBV DNA was confirmed by Southern analysis. The serum HBV virion rapidly decreased by 14 days after HBV DNA transfection of mice treated with asialo-INF-β (10,000 IU), which was in contrast to the increase in the HBV virion levels in the placebo-treated mouse. The conventional IFN-β (10,000 IU) was unable to suppress viremia below the pretreatment level. FIG. 10 summarizes the change of serum HBV virions detected by Southern analysis at the end of treatment (at 14 days after transfection), compared to the pretreatment value (at 7 days after transfection) in each individual athymic mouse. The conventional IFN-β (1,000 or 10,000 IU) did not demonstrate a statistically significant antiviral effect compared to the placebo (P>0.05; placebo versus conventional IFN-β by Bonferroni t tests). This negative result is in contrast to asialo-INF-β (10,000 IU), which produced a statistically significant antiviral effect (P<0.005, asialo-INF-β versus placebo or 1,000 IU of conventional IFN-β; and P<0.05, asialo-INF-β versus 10,000 IU of conventional IFN-β by Bonferroni t tests after significant ANOVA). The viremia was also suppressed below the pretreatment level in some mice at smaller dose of asialo-INF-β (1,000 IU), but statistically significant anti-viral effect was not observed at this dose (P>0.05, versus placebo by Bonferroni t tests).

The conventional recombinant mouse IFN-β (1,000 or 10,000 IU) was unable to suppress the viremia below the pretreatment level and did not demonstrate a statistically significant antiviral effect compared to the placebo (P>0.05; placebo versus conventional IFN-β by Bonferroni t tests). In contrast, asialo-IFN-β (1,000 or 10,000 IU) produced a statistically significant antiviral effect (P<0.001; asialo-IFN-β versus placebo or conventional IFN-β by Bonferroni t tests after significant ANOVA), and reduced the amount of virus below the pretreatment level (FIG. 10). Of note, the virus was completely eradicated and not detectable in one of three and two of three mice at the end of treatment with 1,000 or 10,000 IU of asialo-IFN-β, respectively.

In addition, the greater effectiveness of asialo-IFN-β relative to conventional IFN-β in vivo was confirmed by Southern analysis of PCR products using the HBV-specific restriction fragment.

The experiment in this section demonstrated that the ASGP receptor-mediated augmentation of the antiviral effect of IFN in vitro and in vivo. A significantly greater antiviral effect was produced by asialo-IFN compared with conventional IFN-α or β (FIG. 5).

Compared to the IFN-α/β receptor with 100–5,000 binding sites per cell, the ASGP receptor is an abundant receptor with as many as 50,000–500,000 binding sites per hepatocyte. Enhanced efficacy of this modified IFN clearly requires binding to ASGP receptor as evidenced by competitive inhibition studies (FIG. 8). More importantly, the binding of asialo-IFN-β to IFN receptor is essential for its antiviral effect (FIG. 9).

Furthermore, 2–5A synthetase was induced by asialo-IFN-β at a level significantly higher than by conventional IFN-β, confirming the IFN receptor-mediated augmentation of anti-viral effect. These observations are consistent with the hypothesis that the binding of asialo-IFN-β to the ASGP receptor facilitates signaling through an IFN-α/β receptor and augments its antiviral effect.

Use

The animal hepatitis models of the invention can be used for immunological and molecular studies of the pathologic process of hepatitis including studies of liver cell death. Importantly, the model can be used to screen potential therapeutics.

Mutational changes or deletions in the HBV genome have been identified and are believed to be associated with the development of severe forms of hepatitis; however, this hypothesis has not been tested in vivo because of the lack of an appropriate model system. The cellular functions of various HBV transactivator proteins and the possible involvement of these proteins in the cancer process have also not been examined in normal adult hepatocytes. This hypothesis may now be amenable to experimental evaluation using the animal hepatitis model described herein by preparing animals harboring variant or mutant or another virus. In addition, it is now possible to develop experimental models to test the anti-viral effect of therapeutic regimens in vivo and to investigate the pathogenicity of other hepatotrophic viruses, including hepatitis C virus.

Asialo-interferon β can be used to treat hepatitis B (or hepatitis C or hepatitis G) at dosages similar to or less than used by those skilled in the art for the natural form of human interferon. Because of the greater specificity, higher effective dosages will be possible with lower toxicity. Those skilled in the art will be able to determine the proper dosage through the use of animal models and dose escalation clinical trials. Of course, the effective dosage will generally be less than for natural interferon which has not been treated to remove a terminal sialic acid. Other forms of interferon can be treated similarly.

Production of Other Asialoglycoproteins.

Asialoglycoproteins other than IFN can be produced in a manner similar to that described above for IFN. For example, glycosylated cytokines, such as IL-5, IL-6, IL-9, IL-10, IL-12, fibroblast growth factor, nerve growth factor, and platelet-derived growth factor are available from Sigma as catalog nos. I 5273, I 3268, I 3394, I 3519, I 1270, F 3133, N 4273, and P 8184, respectively. These cytokines can then be treated with neuraminidase to produce asialocytokines as described above.

What is claimed is:

1. A method of treating viral hepatitis in a mammal, the method comprising administering to the mammal a composition comprising a therapeutic amount of asialointerferon-β.

2. A method of treating viral hepatitis in a mammal, the method comprising confirming that the mammal has viral hepatitis, and administering to the mammal a composition comprising a therapeutic amount of asialointerferon-β.

3. The method of claim 2, wherein the confirming step comprises measuring the level of hepatitis virus replication in the mammal.

4. The method of claim 3, wherein the level of hepatitis virus replication is measured using a hepatitis virus-specific polymerase chain reaction.

5. The method of claim 3, wherein the level of hepatitis virus replication is measured by detecting hepatitis viral antigen in a bodily fluid of the mammal.

6. The method of claim 5, wherein the bodily fluid is blood.

7. The method of claim 5, wherein the hepatitis viral antigen is the hepatitis B e antigen (HBeAg).

8. The method of claim 1, wherein the viral hepatitis is caused by hepatitis B virus infection.

9. The method of claim 1, wherein the viral hepatitis is caused by hepatitis C virus infection.

10. The method of claim 1, wherein the composition is administered subcutaneously, intramuscularly, intraarterially, or intravenously.

11. The method of claim 10, wherein the therapeutic amount is about 0.02 μg to 200 μg/kg body weight/day.

12. The method of claim 11, wherein the therapeutic amount is about 30 μg to 75 μg/day.

13. The method of claim 1, wherein the composition further comprises a pharmaceutically acceptable excipient.

14. The method of claim 13, wherein the excipient is selected from the group consisting of dextrose, an albumin, sodium chloride, a sodium phosphate, and water.

15. The method of claim 10, wherein the therapeutic amount is about 10,000 to 200,000 IU/kg body weight/day.

16. The method of claim 2, wherein the mammal is a human.

17. The method of claim 1, wherein the mammal is a human.

18. The method of claim 17, wherein the asialointerferon-β is human asialointerferon-β.

19. The method of claim 2, wherein the confirming step comprises detecting the presence of an antibody against a hepatitis viral antigen in the mammal.

20. The method of claim 19, wherein the hepatitis viral antigen is a hepatitis B viral antigen.

21. The method of claim 20, wherein the hepatitis B viral antigen is the hepatitis B e antigen (HBeAg).

22. The method of claim 1, wherein the viral hepatitis is caused by hepatitis G virus infection.

23. The method of claim 16, wherein the asialointerferon-β is human asialointerferon-β.

* * * * *

UNITED STATES PATENT AND TRADEMARK OFFICE
CERTIFICATE OF CORRECTION

PATENT NO.   : 6,296,844 B1
DATED        : October 2, 2001
INVENTOR(S)  : Hiroshi Takahashi It is certified that error appears in the above-identified patent and that said Letters Patent is hereby corrected as shown below:

Column 3,
Line 65, replace "IFN-βby" with -- IFN-β --.

Column 4,
Line 52, replace "62" with -- β --.

Column 5,
Line 5, replace "62" with -- β --.
Line 21, delete "$^{31}$".
Line 41, replace "IFN-αprobably" with -- IFN-α, probably --.

Column 7,
Line 1, replace "-N+nylon" with -- NT_nylon --.

Column 10,
Line 36, replace "-βwas" with -- -β was --.
Line 60, replace "calorimetric" with -- colorimetric --.

Column 11,
Line 45, replace "(100IU/β1)" with -- (100 IU/µ1) --.

Column 13,
Line 42, replace "[α$^{-x}$P]" with -- [α$^{-33}$P] --.

Column 15,
Line 20, replace "62" with -- β --.

Signed and Sealed this

Fifth Day of November, 2002

Attest:

JAMES E. ROGAN
Attesting Officer    Director of the United States Patent and Trademark Office